United States Patent
Goto

(10) Patent No.: US 8,491,463 B2
(45) Date of Patent: Jul. 23, 2013

(54) ENDOSCOPE TREATMENT SYSTEM

(75) Inventor: Hiroaki Goto, Tokyo (JP)

(73) Assignee: Olympus Medical Systems Corp. (JP)

( * ) Notice: Subject to any disclaimer, the term of this patent is extended or adjusted under 35 U.S.C. 154(b) by 942 days.

(21) Appl. No.: 12/277,508

(22) Filed: Nov. 25, 2008

(65) Prior Publication Data
US 2009/0137867 A1    May 28, 2009

(30) Foreign Application Priority Data
Nov. 28, 2007   (JP) .............................. P2007-307687

(51) Int. Cl.
*A61B 1/00* (2006.01)

(52) U.S. Cl.
USPC ........... 600/104; 600/106; 600/127; 600/129; 606/32; 606/46

(58) Field of Classification Search
USPC ................................. 600/127, 129
See application file for complete search history.

(56) References Cited

U.S. PATENT DOCUMENTS

| | | | | |
|---|---|---|---|---|
| 3,910,279 A | * | 10/1975 | Okada et al. | 606/47 |
| 5,415,656 A | | 5/1995 | Tihon et al. | |
| 5,897,487 A | * | 4/1999 | Ouchi | 600/127 |
| 6,059,719 A | * | 5/2000 | Yamamoto et al. | 600/127 |
| 6,699,180 B2 | * | 3/2004 | Kobayashi | 600/127 |
| 7,101,378 B2 | | 9/2006 | Salameh et al. | |
| 2004/0092953 A1 | | 5/2004 | Salameh et al. | |
| 2004/0210111 A1 | * | 10/2004 | Okada | 600/127 |

FOREIGN PATENT DOCUMENTS

| | | |
|---|---|---|
| JP | H8-509894 | 10/1996 |
| JP | 2002-112946 | 4/2002 |
| JP | 2004-73582 | 3/2004 |
| WO | WO 2004/041329 A2 | 5/2004 |

OTHER PUBLICATIONS

Search Report issued by European Patent Office in connection with corresponding application No. EP 08 02 0533 on May 14, 2009.
Japanese Office Action mailed Jul. 17, 2012 in connection with corresponding Japanese Patent Application No. 2007-307687 and English translation thereof.
Japanese Office Action mailed Jul. 10, 2012 in connection with corresponding Japanese Patent Application No. 2007-307687 and English translation thereof.

* cited by examiner

*Primary Examiner* — Matthew J Kasztejna
(74) *Attorney, Agent, or Firm* — Ostrolenk Faber LLP

(57) ABSTRACT

An endoscope treatment system includes: an endoscope; and a treatment tool that has a sheath that is inserted in a channel of an insertion portion of the endoscope, in which projection portions that project outward from the sheath in the radial direction are provided, and engagement portions that engage the projection portions are provided near the channel of the endoscope.

5 Claims, 8 Drawing Sheets

ENDOSCOPE TREATMENT SYSTEM

BACKGROUND OF THE INVENTION

1. Field of the Invention

The present invention relates to an endoscope treatment system that uses in combination with an endoscope, a treatment tool that is inserted in a channel of this endoscope, and an overtube that covers an insertion portion of the endoscope or a cap for the endoscope and the like.

Priority is claimed on Japanese Patent Application No. 2007-307687, filed Nov. 28, 2007, the content of which is incorporated herein by reference.

2. Description of Related Art

Conventionally, as a treatment tool that is used in combination with an endoscope, for example a treatment tool for incising a living tissue, there is known one that houses a wire that forms a knife portion in a flexible sheath, or disposes it along the outer surface of the peripheral wall of a flexible sheath, and when actually incising the living tissue, causes a portion of the wire to expand in diameter so as to greatly project to the outside of the flexible sheath, and in this state, by pressing the wire against the required portion of the living tissue that is to be incised while passing a high-frequency current through the wire, thereby making an incision (for example, refer to Published Japanese translation No. H8-509894 of PCT International Publication, and Japanese Unexamined Patent Application, First Publication No. 2004-73582).

SUMMARY OF THE INVENTION

The endoscope treatment system according to a first aspect of the present invention includes: an endoscope; and a treatment tool that has a sheath that is inserted in a channel of an insertion portion of the endoscope, in which projection portions that project outward from the sheath in the radial direction are provided, and engagement portions that engage the projection portions are provided near the channel of the endoscope.

The endoscope treatment system according to a second aspect of the present invention includes: an endoscope; a cap that is attached to the distal end of an insertion portion of the endoscope in a non-rotatable manner with respect to the insertion portion; and a treatment tool that has a sheath that is inserted in a channel of the insertion portion of the endoscope, in which projection portions that project outward from the sheath in the radial direction are provided, and engagement portions that engage the projection portions are provided in the cap.

The endoscope treatment system according to a third aspect of the present invention includes: an endoscope; an overtube that covers an insertion portion of the endoscope, and a sheath that is inserted in a channel of the insertion portion of the endoscope, in which projection portions that project outward from the sheath in the radial direction are provided, and engagement portions that engage the projection portions are provided in the distal end of the overtube.

Also, in the endoscope treatment system according to the present invention, it is preferable that the engagement portions be slots that engage the projection portions in an inserted state.

Also, in the endoscope treatment system according to the present invention, it is preferable that the projection portions and the engagement portions rotate in conjunction with the rotation operation of the insertion portion of the endoscope.

Also, in the endoscope treatment system according to the present invention, it is preferable that the projection portions freely project and retract.

Also, in the endoscope treatment system according to the present invention, it is preferable that the projection portions be conductive wires to which high-frequency electricity is supplied.

Also, in the endoscope treatment system according to the present invention, it is preferable that the cap be transparent.

Also, in the endoscope treatment system according to the present invention, it is preferable that the cap be formed in a tapered shape that gradually narrows toward its distal end portion.

DETAILED DESCRIPTION OF THE INVENTION

Hereinbelow, the embodiments of the present invention will be described.

Figure 1:
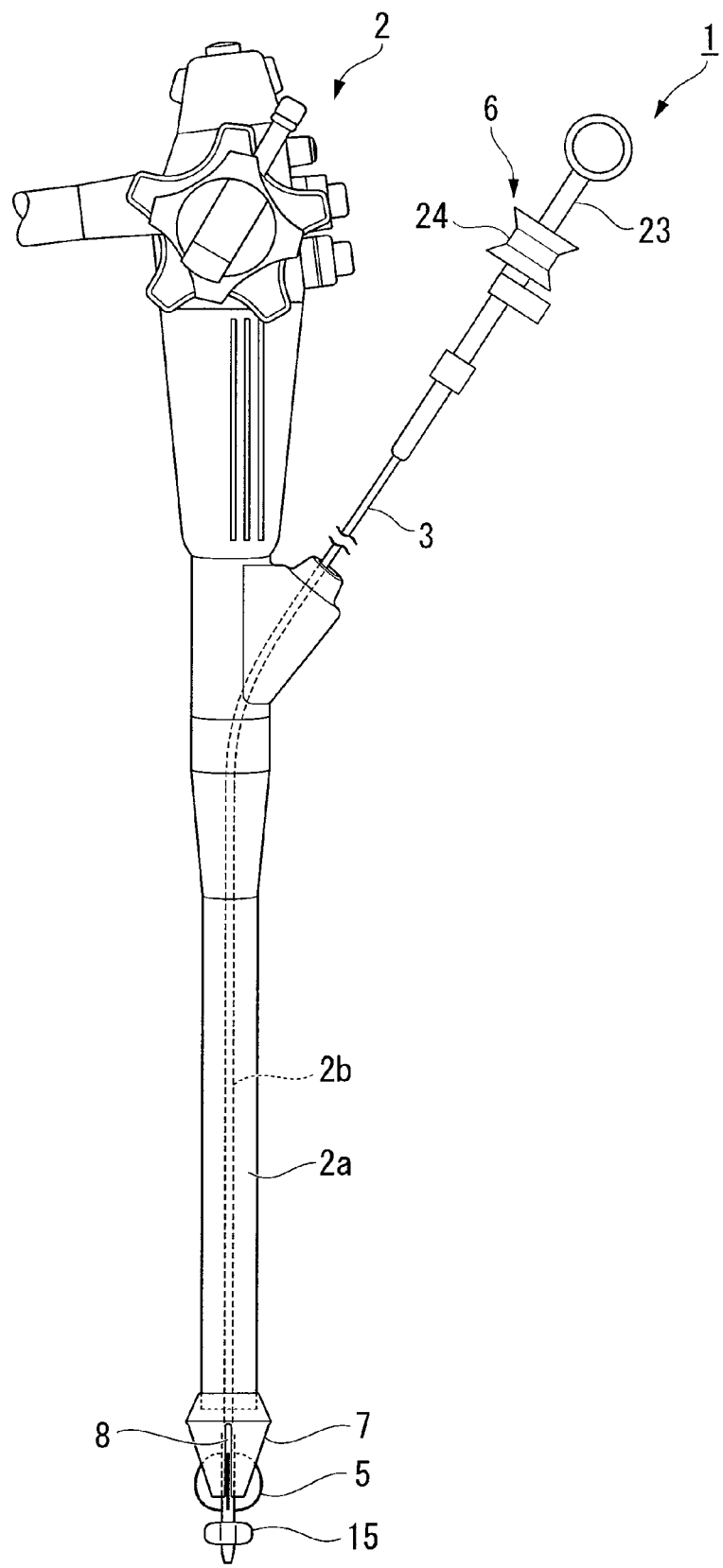
FIG. 1 is a perspective view that shows an endoscope treatment system of a first embodiment of the present invention.
Figure 2:
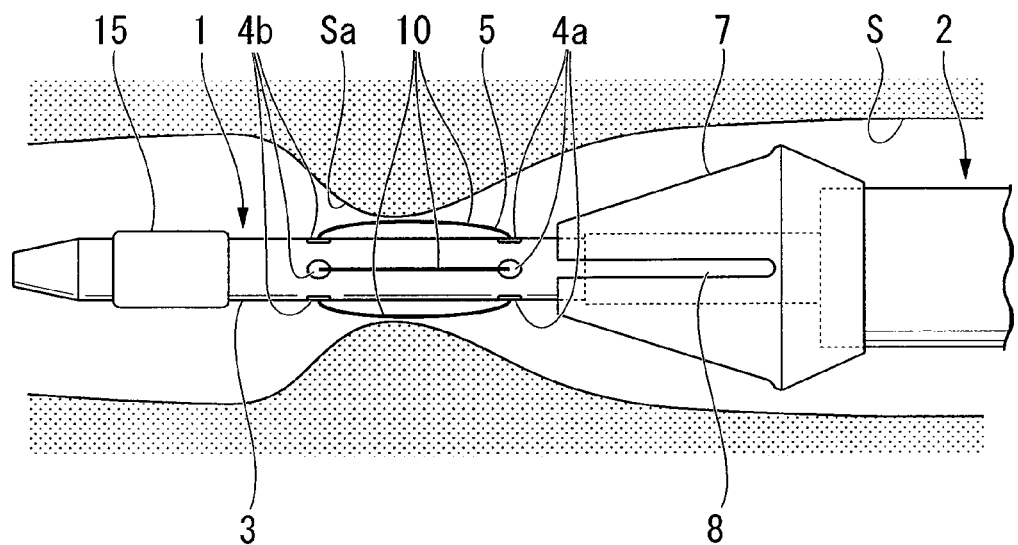
FIG. 2 is a side view that shows a distal end portion of the endoscope treatment system.
Figure 3:
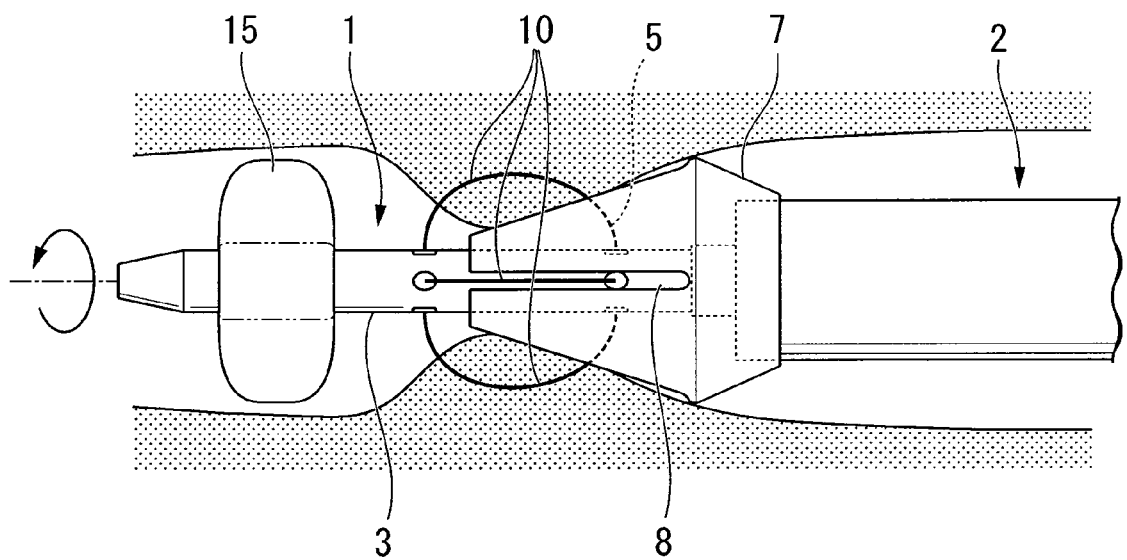
FIG. 3 is a side view that shows the state of incising a narrow portion of an esophagus by the endoscope treatment system.

FIG. 1 to FIG. 8 show an embodiment of an endoscope treatment system according to the present invention. Among these drawings, FIG. 1 is an overall perspective view of an endoscope treatment system that shows the state of a treatment tool incorporated in an endoscope with a distal end cap, FIG. 2 is a side view that shows the distal end portion of the endoscope treatment system, and FIG. 3 is a side view that shows the state of incising a narrow portion of an esophagus by the endoscope treatment system.

The endoscope treatment system of this embodiment is provided with an endoscope 2, a cap 7 that is attached to the distal end of an insertion portion 2a of the endoscope 2 in a non-rotatable manner with respect to the insertion portion 2a, and a treatment tool 1 for incision that has a flexible sheath 3 that is inserted in a channel 2b of the insertion portion 2a of the endoscope 2.

The treatment tool for incision 1 is used by being incorporated in the endoscope 2 as shown in FIG. 1. The treatment tool 1, as shown in FIG. 1 and FIG. 2, is provided with the flexible sheath 3 (sheath) that is inserted into the channel 2b formed in the insertion portion 2a of an endoscope 2, a plurality of wires 5 (projection portions) that are inserted in the flexible sheath 3, and an operation portion 6 that is connected to one end of the wires 5. The flexible sheath 3 is made of, for example, a coil sheath, has flexibility, and has an insertion hole 3a that extends along the axis in the interior. The wires 5 are respectively inserted in first wire insertion holes 4a that are provided at the distal end portion of the flexible sheath and second wire insertion holes 4b that are provided further to the distal end side of the flexible sheath than the first wire insertion holes 4a. Thereby, a portion of the wires 5 becomes wire exposed portions 10 by being exposed outward of the flexible sheath 3. By relatively advancing and retracting the operation portion 6 in the longitudinal direction of the wires 5 with respect to the flexible sheath 3, the length of the exposed portions 10 of the wires that are exposed outward of the flexible sheath 3 is adjusted.

Note that here the side at which the operation portion 6 is disposed in the treatment tool 1 is referred to as the proximal end side, and the opposite side is referred to as the distal end side.

Here, the first wire insertion holes 4a and the second wire insertion holes 4b that are formed in the flexible sheath 3 and through which the plurality of wires 5 are inserted are formed for each wire 5. That is, the first wire insertion holes 4a and the second wire insertion holes 4b are formed in the same number as that of the wires 5. Here, the first wire insertion holes 4a are formed at the same position in the longitudinal direction of the flexible sheath 3, and the second wire insertion holes 4b are formed at the same position in the longitudinal direction of the flexible sheath 3. Also, these first and second wire insertion holes 4a, 4b are formed at equal intervals in the circumferential direction.

Figure 4:
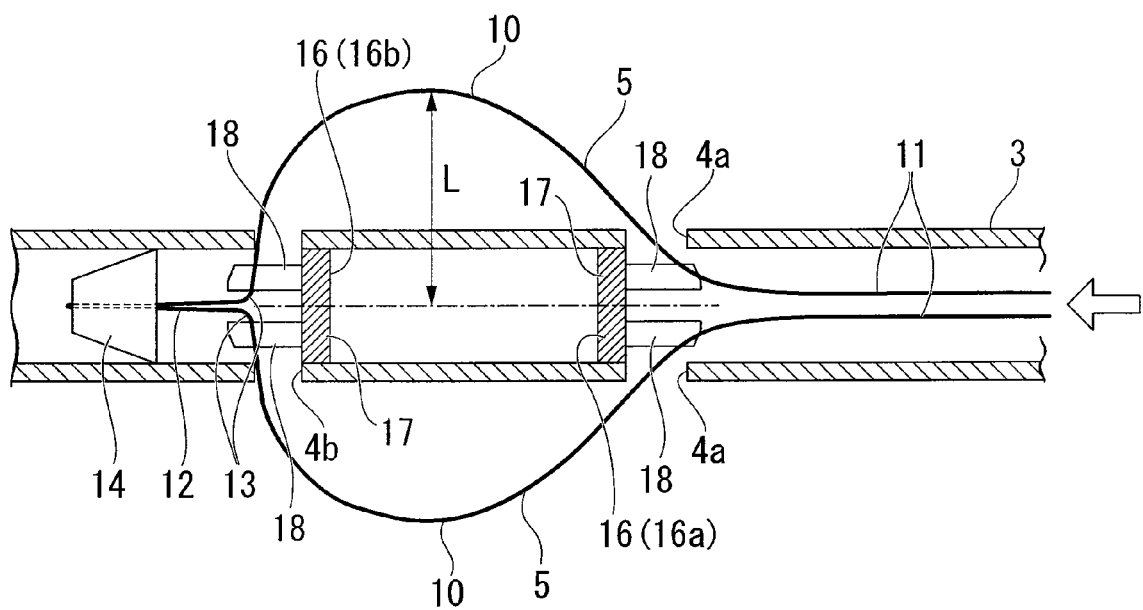
FIG. 4 is a sectional view that shows an internal construction of a distal end portion of a flexible sheath that is used in the endoscope treatment system.

The plurality of wires 5, as shown in FIG. 4, each have a proximal end side insertion portion 11 that passes through the interior space of the flexible sheath 3 further to the proximal end side than the first wire insertion hole 4a, the exposed portion 10 that extends from this proximal end side insertion portion 11 toward the distal end side, passes through the first wire insertion hole 4a, and is exposed outward of the flexible sheath 3, a distal end side insertion portion 12 that extends from this exposed portion 10 toward the distal end, passes through the second wire insertion hole 4b, and again enters into the interior space of the flexible sheath 3, and a bend portion 13 that is provided at the end portion of the exposed portion 10 side of this distal end side insertion portion 12 and bends the wire 5 from the direction of entering into the interior space of the flexible sheath 3 via the second wire insertion hole 4b to the axial direction of the flexible sheath 3. Also, the plurality of wires 5 are bundled into one by a binding member 14 at a position further to the distal end side than the bend portion 13.

The wires 5 have flexibility, and when the operation portion 6 is operated to be advanced or retreated in the longitudinal direction of the wires, as shown in FIG. 2 and FIG. 3, the shape of the exposed portions 10 is deformed so as to swell outward or contract inward. Also, the wires 5 have electrical conductivity, and so by supplying high-frequency electrical current, the exposed portions 10 function as a knife portion that incises a living tissue (specifically, an inner wall of the esophagus).

The binding member 14 has a hole in the center, and the wires 5 are inserted into this hole. These wires 5 are engaged and fixed to the binding member 14 by the frictional force due to the elasticity of the binding member itself or an adhesive.

The binding member 14 is formed in a tapered shape in which the distal end side narrows, and made of a material that has suitable elasticity and heat resistance. Also, the maximum diameter of the binding member 14 is set to a value that is slightly larger than the inner diameter of the flexible sheath 3 such that the binding member 14 is engaged with the inner surface of the flexible sheath 3 with a suitable frictional force.

A balloon 15 which is capable of attaining a greater diameter than the diameter of the flexible sheath 3 is attached further to the distal end side than the wire exposed portions 10. The balloon 15 is connected to an air supply source via an air pipe (not illustrated) that is disposed in the flexible sheath 3, and so when air is supplied from this air pipe to the interior, as shown in FIG. 3, it swells toward the outside.

As shown in FIG. 5A to FIG. 5D, the number of the wires 5 may be 4, 3, 2, or 8, or a plurality other than that. However, as shown in these drawings, the wire exposed portions 10 are disposed in an equiangular arrangement in the circumferential direction so as to form a radial pattern.

A heat-resistant coating is applied to the wire 5 near the first wire insertion holes 4a and the second wire insertion holes 4b in order that the heat of the wires 5 is not directly transferred to stabilizers 16 and cap 7 described below.

As shown in FIG. 4, in the flexible sheath 3, the stabilizers 16 are provided near the first and second wire insertion holes 4a, 4b. When the exposed portions 10 of the wires 5 are expanded in diameter, the stabilizers 16 restrict the movement of the wires 5 so that the wires 5 extend in the normal line direction with respect to the outside surface of the flexible sheath 3 without twisting to the right and left, that is, so as not to shift from the radial direction of the flexible sheath 3.

Various types of the stabilizers 16 are conceivable. For example, as shown in FIG. 4, stabilizers 16a and 16b of the same shape may be disposed inside of the flexible sheath 3 so as to be mutually symmetrical in correspondence with the first and second wire insertion holes 4a and 4b, and be fixed by a suitable fixing means such as an adhesive or press fitting.

The proximal end side stabilizer 16a corresponding to the first wire insertion holes 4a has a disk portion 17 and four projections 18 having a fan shaped cross-sectional that extend in a direction perpendicular to the disk portion 17 from one side surface of the disk portion 17, with the projections 18 being disposed and fixed so as to face the proximal end side. Also, the distal end side stabilizer 16b corresponding to the second wire insertion holes 4b has a disk portion 17 and four projections 18 having a fan shaped cross-sectional that extends in a direction perpendicular to the disk portion 17 from one side surface of the disk portion 17, with the projections 18 being disposed and fixed so as to face the distal end side.

Also, wire guide slots are respectively formed between the projections 18. The stabilizers 16a and 16b are disposed and fixed in the flexible sheath 3 so that the wire guide slots of the proximal end side stabilizer 16a and the wire guide slots of the distal end side stabilizer 16b mutually have the same angle positions and correspond to the first and second wire insertion holes 4a, 4b. Also, the diameter of the wire guide slots is set to be slightly greater than the diameter of the wires 5.

Note that these stabilizers 16a and 16b are made of a material having a suitable rigidity, for example, a metal or a hard plastic.

Figure 6A:
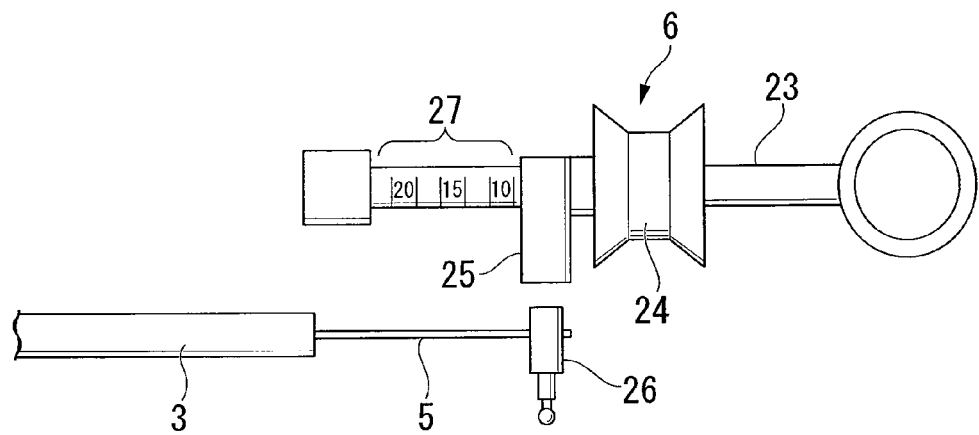
FIG. 6A is an exploded side view of an operation portion that is used in the endoscope treatment system.
Figure 6B:
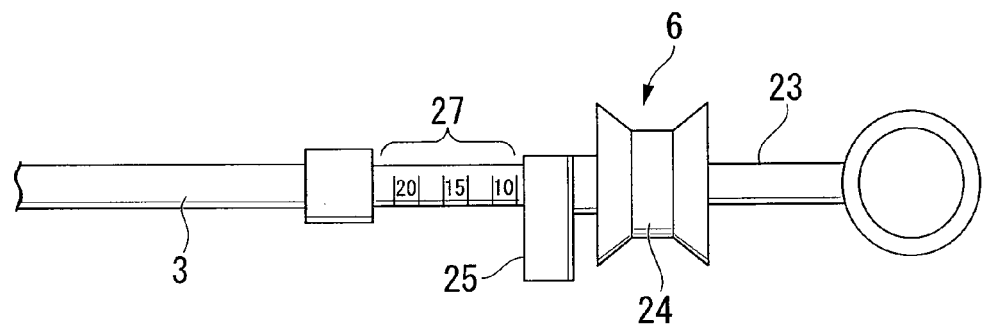
FIG. 6B is a side view of the operation portion that is used in the treatment tool.

FIG. 6A is an exploded view of the operation portion 6, and FIG. 6B is a side view of the operation portion 6. As shown in these drawings, the proximal end of the flexible sheath 3 is connected to an operation portion main body 23. A guide slot which is not illustrated is formed in the axial direction in the intermediate portion of the operation portion main body 23, and a slide portion 24 that slides along the guide slot is mounted on the operating section main body 23. A terminal supporting portion 25 is integrally provided at the slide portion 24, and an electrode terminal 26 is attached to this terminal supporting portion 25. The proximal ends of the wires 5 are connected to the electrode terminal 26, and a connection terminal (not illustrated) that extends from a high-frequency power source is capable of being connected to this electrode terminal 26.

The plurality of wires 5 may individually extend toward the proximal end to be connected to the electrode terminal 26. The plurality of wires 5 may be gathered into one at the proximal end side and be connected to the electrode terminal 26.

Also, a scale 27 is affixed to the operation portion main body 23, and with this scale 27, the amount of movement of the slide portion 24, and as a result, a guide of the clearance L of the exposed portions 10 of the wires 5 from the axis of the flexible sheath 3 can be displayed (refer to FIG. 4).

Here, when the slide portion 24 is advanced or retreated in the longitudinal direction of the wires 5, the proximal end side of the wires 5 that is connected to the electrode terminal 26 that moves integrally with the slide portion 24 moves in the same direction. The movement of these wires 5 is in turn transmitted to the distal end side, and as a result the length of the exposed portions 10 of the wires is adjusted as shown in FIG. 4. That is, the operation portion main body 23 and the slide portion 24 constitute the operation portion 6 that adjusts the length of the exposed portions 10 of the wires by advancing or retracting the wires 5.

Figure 7:
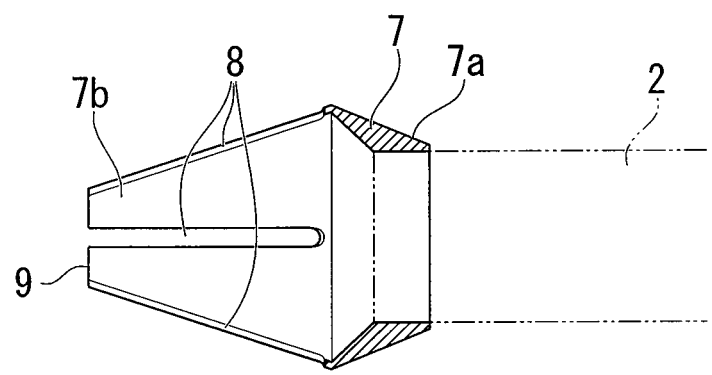
FIG. 7 is a sectional view of a cap that is used in the endoscope treatment system.
Figure 8:
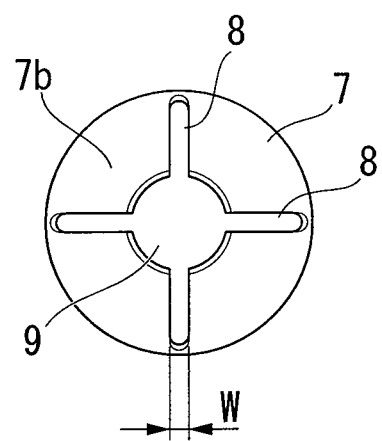
FIG. 8 is a front view of the cap that is used in the endoscope treatment system.

As shown in FIG. 7 and FIG. 8, the cap 7 is attached to the distal end of the endoscope 2 in a non-rotatable manner. Methods of attaching the cap 7 to the distal end of the endoscope 2 may include one that employs a screw or one that uses a concavo-convex fitting. However, it is necessary that the cap 7 is attached to the endoscope 2 in a non-rotatable manner. The cap 7 is formed in a tapered shape that gradually narrows from a proximal end portion 7a that is attached to the distal end of the endoscope 2 to the distal end portion.

Slots 8 (engagement portions) that cause the wires 5 of the treatment tool 1 to engage are formed in a tapered portion 7b of the distal end of the cap 7 so as to extend along the axis of the cap 7 to the distal end thereof. The slots 8 are provided in the same number as that of the wire 5, that is, in the case of there being four of the wires 5, four slots 8 are provided. The width dimension w of each of the slots 8 is set so as to be 2 to 7 times as large as the diameter of the wire 5, and more preferably 3 to 6 times. When the width dimension of the slot 8 is too narrow, the engagement of the wire by the slot 8 is hindered. Also, when the width dimension of the slot 8 is too wide, the function of guiding the wire 5 by the slot 8 is impaired.

Also, the cap 7 is preferably made of a transparent material. With this cap 7, a procedure that uses the endoscope is not affected with no blocking of the field of view of the endoscope.

Note that an opening 9 that allows passage of the sheath 2 is formed in the center of the distal end of the cap 7.

Next, the procedure of incising a narrow portion of an esophagus using the endoscope treatment system of the above constitution will be described.

First, as shown in FIG. 2, the exposed portions 10 of the wires are put into a state of their most contracted diameter, and the balloon 15 is put in a contracted state. Then, the insertion portion 2a of the endoscope 2 with the cap 7 attached to the distal end thereof in advance is inserted into the mouth and guided to the interior of the esophagus S, with the narrow portion Sa being confirmed by endoscopic images. After confirming the location of the narrow portion Sa, the flexible sheath 3 is inserted in the channel 2b of the endoscope 2. Then, while confirming with the endoscopic images, the flexible sheath 3 is projected from the distal end of the insertion portion 2a.

Then, as shown in FIG. 2, while performing confirmation with endoscopic images, the exposed portions 10 of the wires are made to face the narrow portion Sa of the esophagus. Adjustment of the position of the exposed portions 10 of the wires and the narrow portion Sa may be performed by adjusting the insertion amount of the insertion portion 2a of the endoscope while maintaining the relative positions of the endoscope 2 and the treatment tool 1 constant. Alternatively, the insertion amount of the insertion portion 2a of the endoscope may be left as is and the projection amount of the flexible sheath 3 from the distal end of the insertion portion 2a may be adjusted.

After the exposed portions 10 of the wires are made to oppose the narrow portion Sa of the esophagus in the manner, the slider portion 24 of the operation portion 6 is made to advance in the longitudinal direction of the wires to cause the exposed portion 10 of each wire to expand in diameter as shown in FIG. 3. Simultaneously with this, air is supplied via the air pipe (not shown) to inflate the balloon 15.

Here, when the slider portion 24 is made to advance in the longitudinal direction of the wires, the proximal end side of the wires 5 that are connected to the slider portion 24 move in the same direction, and the movement of the wires 5 is in turn transmitted to the distal end side, and as a result the distal end side of the wires 5 receives the force to be moved forward. At this time, since the bend portion 13 is provided at the distal end side insertion portion 12 of the wires 5, by this bend portion 13, the transmitted force that causes the wires 5 to move forward is divided. That is, at the distal end side of the wires 5, the bend portion 13 functions as a stopper, and forward movement of the wires 5 further to the front side than the bend portion 13 is restricted. In addition, in this embodiment, forward movement of the wires 5 further to the front side than the bend portion 13 is restricted by the binding member 14 that is supplementarily provided. As a result of these, relative movement of the proximal end side of the wires 5 with respect to the flexible sheath 3 is integrated at the exposed portions 10 of the wires that are exposed outward of the flexible sheath 3, and as shown in FIG. 3, the exposed portions 10 of the wires are expanded in diameter to the desired shape.

Here, the operation of expanding the diameter of the exposed portions 10 of the wires by the operation portion 6 and the operation of inflating the balloon 15 may be interrelated and simultaneously performed.

For example, when advancing the slider portion 24 of the control portion 6, the movement of the slider portion 24 may be detected by a sensor, and based on this detection result, an air supply means which is not illustrated may be activated to supply the predetermined amount of air to the balloon 15 to inflate the balloon 15.

Figure 5A:
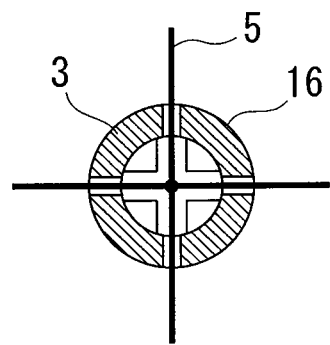
FIG. 5A to FIG. 5D are front views that show arrangement examples of exposed portions of wires that are used in the endoscope treatment system.
Figure 5B:
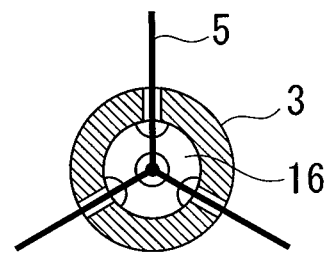
Figure 5C:
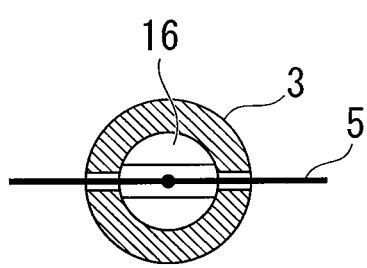
Figure 5D:
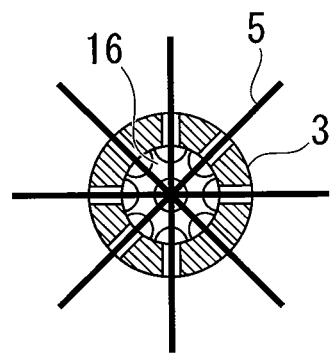
Figure 5E:
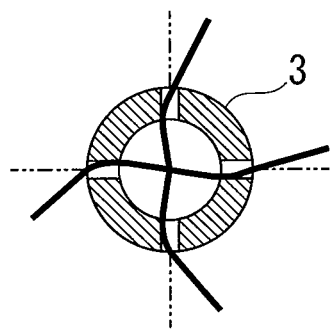
FIG. 5E is a front view of a reference example of the exposed portions of the wires that are used for comparison with the present invention.

Also, the stabilizers 16 are provided in the vicinity of the first wire insertion holes 4a and the second wire insertion holes 4b of the flexible sheath 3. Because the wires 5 are guided by the wire guide slots of the stabilizers 16, as shown in FIG. 5A to FIG. 5D, the exposed portions 10 of the wires 5 expand in diameter so as to extend in the normal line direction with respect to the outside surface of the flexible sheath 3. Accordingly, as shown in FIG. 5E, the exposed portions 10 of the wires 5 expand in diameter while being disposed in an equiangular arrangement in the circumferential direction so as to form a radial pattern without twisting to the right and left. As described below, this state is similarly maintained when rotating this treatment tool 1 to incise the narrow portion Sa of the esophagus.

Also, when the exposed portions 10 of the wires 5 are expanded in diameter to the desired shape, the clearance L of the exposed portions 10 of the wires 5 from the axis of the flexible sheath 3 can be accurately found with the scale 27 that is attached to the operation portion main body 23. For this reason, during operation of the operation portion 6, it is possible to prevent the depth of incision into the narrow portion Sa of the esophagus by the exposed portions 10 of the wires 5 from becoming deeper than required beforehand.

Also, when expanding the diameter of the exposed portions 10 of the wires 5, these wires 5 that have been expanded in diameter are inserted and engaged in the slots 8 of the cap 7. Note that in the case of the positions of the wires 5 and the slots 8 being shifted in the circumferential direction, by rotating the treatment tool 1 relative to the insertion portion 2a of the endoscope 2 so that the wires 5 of the treatment tool 1 arrive at the positions corresponding to the slots 8, the wires 5 will naturally be inserted and engaged in the slots 8.

Note that, to inserte and engage the wires 5 in the slots 8 as described above, from the state shown in FIG. 2, after expanding the diameter of the exposed portions 10 of the wires, the cap 7 may be advanced integrally with the insertion portion 2a relative to the treatment tool 1. Alternatively, by disposing the cap 7 in a position that enables the wires 5 to be engaged in the slots 8 in advance, the exposed portions 10 of the wires 5 may be then expanded in diameter to be engaged.

Expansion of the diameter of the exposed portions 10 of the wires 5 by operation of the operation portion 6 is performed while passing high-frequency current through the wires 5. Accordingly, when the exposed portions 10 of the wires 5 are expanding in diameter, incision of the interior of the narrow portion Sa of the esophagus to the predetermined depth is performed. Then, while flowing high-frequency current to the wires 5, the treatment tool 1 is rotated with the insertion portion 2a of the endoscope 2. At this time, since all the wires 5 integrally rotate with the cap 7 while being guided by the slots 8 of the cap 7, when incising the living tissue, even if a reactive force is received from the living tissue, the exposed portions 10 of the wires 5 stably rotate while being disposed in a radial shape without the wires 5 shifting from the radial direction to twist or bend or collapse in the circumferential direction. Thereby, it is possible to quickly make an incision in the narrow portion Sa of the esophagus.

In this embodiment, since the balloon 15 with the expanded diameter is disposed at the predetermined position in the distal end side of the exposed portions 10 of the wires 5, even in the case of a force in the pull-out direction being suddenly applied during rotation, the balloon 15 that has expanded in diameter functions as an anchor, and so the treatment tool 1 does not shift to the proximal end side. That is, the exposed portions 10 of the wires 5 are held at their respective positions facing the narrow portion Sa of the esophagus.

Also, as stated above, the balloon 15 that has expanded in diameter is at a predetermined position at the distal end side of the exposed portions 10 of the wires 5, and, with this balloon 15, the distal end portion of the flexible sheath 3 is held at approximately the center with respect to the esophagus. Accordingly, when the treatment tool 1 is rotated, it is possible to prevent unexpected swinging of the distal end portion of the flexible sheath 3 including the exposed portions 10 of the wires 5. As a result, it is possible to perform smooth incision of the narrow portion Sa of the esophagus with the exposed portions 10 of the wires 5.

After making the incision, along with contracting the balloon 15, the exposed portions 10 of the wires 5 are contracted by operation of the operation portion 6, and in this state, the distal end portion of the treatment tool 1 is completely housed inside the channel of the endoscope 2, and this treatment tool 1 is pulled out from the body with the endoscope 2.

Note that in the above first embodiment, the balloon 15 and the stabilizers 16 are provided, but these members are not necessarily required, and may be omitted.

Modified Example

Figure 9:
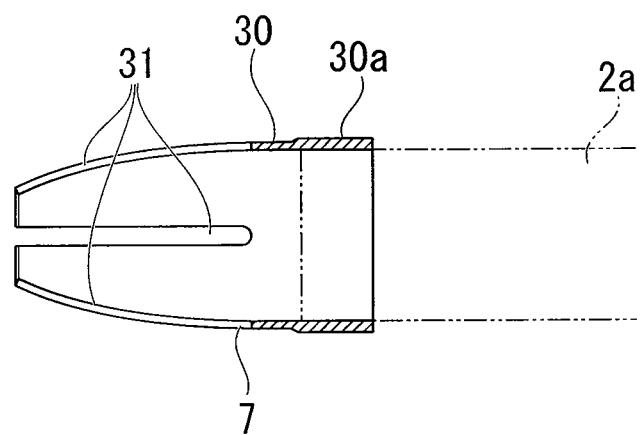
FIG. 9 is a sectional view that shows a modified example of a cap that is used in the endoscope treatment system of the first embodiment of the present invention.

FIG. 9 shows a modified example of the embodiment according to the present invention.

The cap 7 shown in FIG. 7 and FIG. 8 is formed in a tapered shape that gradually narrows from the proximal end portion 7a that is attached to the distal end of the insertion portion 2a of the endoscope 2 to the distal end portion, however, the cap 7 shown here has a tapered, curved shape in which the reduction ratio gradually increases from the proximal end 30a to the distal end portion. Slots 31 for engaging the wires for incision are formed in this cap 30 so as to extend along the axis.

Figure 10:
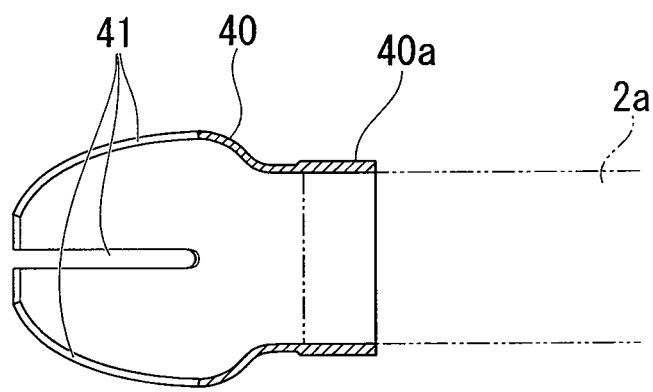
FIG. 10 is a sectional view that shows another modified example of a cap that is used in the endoscope treatment system of the first embodiment of the present invention.

FIG. 10 shows another modified example of the embodiment according to the present invention.

A cap 40 shown here has a curved shape that bulges outward once from a proximal end portion 40a that is attached to the distal end of the insertion portion 2a of the endoscope, and then tapers so that the reduction ratio gradually increases toward the distal end portion. Also, Slots 41 for engaging the wire for incision are formed in this cap 40 so as to extend along the axis. When the cap 40 of this modified example is used, it is possible to widely secure the field of vision of the endoscope. Also, the cap 40 with a large maximum diameter is obtained.

Second Embodiment

Figure 11A:
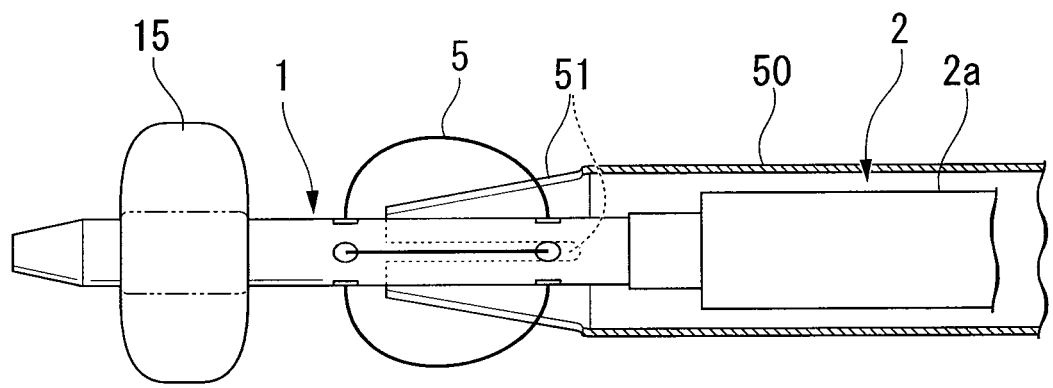
FIG. 11A and FIG. 11B show main portions of an endoscope treatment system of a second embodiment of the present invention, with FIG. 11A being a partial sectional side view that shows a structure of a distal end of an overtube and a distal end of an endoscope, and FIG. 11B being a side view of the distal end of the overtube.
Figure 11B:
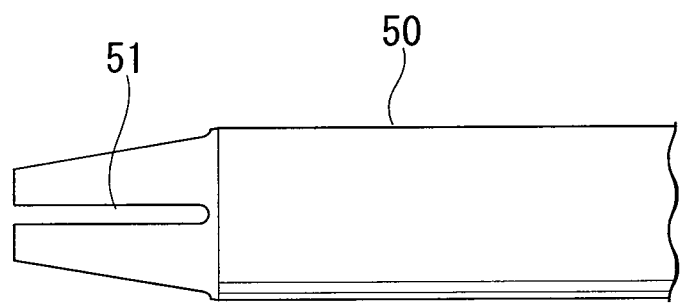

FIG. 11A and FIG. 11B show the main portions of a second embodiment according to the present invention. FIG. 11A is a sectional view that shows distal ends of an endoscope and overtube in a state in which the endoscope is inserted in the overtube, and FIG. 11B is a side view of the distal end of the overtube.

Note that in order to simplify the description, in this second embodiment, constituent elements that are the same as those used in the first embodiment shall be assigned the same reference numerals, and descriptions there of will be omitted.

In this second embodiment, an overtube 50 that covers the insertion portion 2a of the endoscope instead of a cap is provided. Slots 51 (engagement portion) that extend in the axial direction of this overtube 50 are formed at the distal end of the overtube 50.

The wires 5 for incision are inserted and engaged by the slots 51.

With this endoscope treatment system of the second embodiment, when incising a narrow portion of an esophagus, for example, first in the state of the wires 5 for incision being engaged in the slot 51 of the overtube 50, the wires 5 for incision are arranged at a position facing the narrow portion. Then, the overtube 50 is made to rotate about the axis. Thereby, since the wires 5 for incision rotate integrally with the overtube 50 while being guided by the slots 51 of the overtube 50, even in the case of receiving a reactive force from the living tissue, the exposed portions 10 of the wires 5 stably rotate while being disposed in a radial shape without the wires 5 shifting from the radial direction to twist or bend or collapse in the circumferential direction. Thereby, it is possible to quickly make an incision in the narrow portion Sa of the esophagus.

Note that the present invention is not limited to the above embodiments, and design modified examples can be made in the scope of not departing from the spirit of the invention.

In the first and second embodiments, as a member that is made to be engaged in the slots of a cap or overtube, a conductive wire that serves as an incision knife is illustrated, but is not limited thereto, and another treatment tool may be employed. Provided it is one that projects outward in the radial direction from the sheath, it can be applied to the endoscope treatment system of the present invention regardless of whether it is provided in a fixed manner or in a manner capable of protruding and retreating from the sheath.

Also, in the first and second embodiments, slots provided in the cap or the like are used when engaging the projection portions (wires) that project from the sheath to the outside in the radial direction in the cap or overtube, but the present invention is not limited thereto. For example, it is possible to make the projection portions engage with protrusions or depressions provided in the cap or overtube.

Also, in the first and second embodiments, the engagement portions that engage the projection portions are provided in the cap or the overtube, but the present invention is not limited thereto. The engagement portions may be provided in another member, for example a transparent hood that is attached to the distal end of the insertion portion of the endoscope. The bottom line is, the engagement portions that engage the projection portions need only be provided near the channel of the endoscope.

While preferred embodiments of the invention have been described and illustrated above, it should be understood that these are exemplary of the invention and are not to be considered as limiting. Additions, omissions, substitutions, and other modified examples can be made without departing from the spirit or scope of the present invention. Accordingly, the invention is not to be considered as being limited by the foregoing description, and is only limited by the scope of the appended claims.

According to the endoscope treatment system of the present invention, since the projection portions that project outward from the sheath in the radial direction are made to be engaged by the engagement portions that are provided near the channel of the endoscope, it is possible to obviate an occurrence of twisting or bending of the projection portions by shifting from the radial direction, and possible to hold the projection portions in the desired shape.

According to the endoscope treatment system of the present invention, since the projection portions that project outward from the sheath in the radial direction are made to be engaged by the cap of the endoscope, it is possible to obviate an occurrence of twisting or bending of the projection portions by shifting from the radial direction. Also, for example, in the state of the insertion portion of the endoscope being inserted into a body cavity, when the insertion portion of this endoscope is rotated, the cap that is attached to the distal end of the insertion portion integrally rotates, and moreover the projection portions that are engaged by this cap also rotate integrally. That is, since it is possible to make the projection portions that project outward from the sheath in the radial direction integrally rotate with the cap of the endoscope, it is possible to prevent the projection portions from suddenly falling when rotating.

According to the endoscope treatment system of the present invention, since the projection portions that project outward from the sheath in the radial direction are made to be engaged by the overtube, it is possible to obviate an occurrence of twisting or bending of the projection portions by shifting from the radial direction. Also, when for example rotating the overtube about its axial line, it is possible to also cause the projection portions that are engaged at the distal end of this overtube via the engagement portions to integrally rotate. That is, it is possible to rotate the projection portions integrally with the overtube while engaging the projection portions at the outer portions in the radial direction thereof, and therewith it is possible to stably rotate the projection portions.

According to the endoscope treatment system of the present invention, to engage the projection portions in the slots, it is sufficient to simply insert the projection portions in the slots, and the engagement operation of the projection portions becomes simple. Also, it is sufficient to simply form slots as engagement portions, and the processing of the cap is simplified.

According to the endoscope treatment system of the present invention, when the insertion portion of the endoscope rotates, the projection portions and the engagement portions rotate in conjunction with the rotation operation of this insertion portion. In this way, to rotate the projection portions, it is sufficient to simply rotate the insertion portion of the endoscope, and the rotation operation of the projection portions is simplified. Also, when observing the image of the endoscope on a display, the projection portions are disposed near a predetermined position on the screen, and so position of the projection portions is easily confirmed.

According to the endoscope treatment system of the present invention, for example when inserting the endoscope and treatment tool in a body cavity, the projection portions are placed in a contracted state without projecting outward from the sheath in the radial direction. After being inserted to the predetermined position in the body cavity, when the treatment is performed, the projections portions are projected outward in the radial direction and are engaged in the engagement portions of the cap or the overtube. In this way, it is possible to use the projection portions by causing them to project outward in the radial direction as necessary, and so the operation when inserting them in the body cavity becomes easy.

According to the endoscope treatment system of the present invention, it is possible to utilize the conductive wires as an incision knife.

According to the endoscope treatment system of the present invention, even in the case of attaching the cap to the distal end of the endoscope, a procedure that uses the endoscope is not affected, with no blocking of the field of view of the endoscope by this cap.

According to the endoscope treatment system of the present invention, since the tapered portion at the distal end of the cap functions as a guide portion when being inserted in the body cavity, insertion becomes easy. Also, by providing the engagement portions along the tapered shape, it is possible to change the radius of the engagement position corresponding to the projection portion. That is, in the case of the engagement position of the engagement portion to the projection portion being at the distal end side of the cap, it is possible to engage a comparatively smaller radius of the projection portion, and on the contrary in the case of being engaged at the proximal end side of the cap, it is possible to engage a comparatively larger radius of the projection portion.

According to the present invention, since the projection portions that project outward from the sheath in the radial direction are engaged at the cap or overtube, it is possible to obviate an occurrence of twisting or bending of the projection portion by shifting from the radial direction. Also, when for example rotating the endoscope or overtube about its axial line, it is possible to also cause the projection portions that are engaged at the distal end of the cap provided at the distal end of the endoscope or the distal end of the overtube via the engagement portions to integrally rotate, and for this reason it is possible to stably rotate the projection portions. In addition, in the case of providing the incising portion at the distal end of the overtube, the incision operation is simplified due to large rotary torque being obtained.

What is claimed is:

1. An endoscope treatment system comprising:
    an endoscope; and
    a treatment tool that has a sheath configured to be inserted in a channel of an insertion portion of the endoscope;
    wherein projection portions, that project outward from the sheath in a radial direction, are provided,
    an engagement portion that engages the projection portions is provided near the channel of the endoscope;
    the projection portions are exposed outward of the sheath by respectively passing outward of the sheath through a first hole portion, which is formed at a proximal end of the sheath, and the projection portions respectively re-enter into the sheath by passing into the sheath through a second hole portion, which is formed at a distal end of the sheath, multiple first hole portions being positioned on a same location of the sheath and spaced from each other in a circumferential direction of the sheath, and multiple second hole portions being positioned on a same location of the sheath and spaced from each other in a circumferential direction of the sheath, and
    the engagement portion has a tapered portion which is formed in a tapered shape such that a diameter thereof gradually narrows to a distal end portion thereof,
    slots in which the respective projection portions are capable of being protruded are formed with the tapered portion, and
    an outer diameter of the tapered portion, which includes at least a part of the slots, at a distal end side thereof is smaller than an outer diameter of the projection portions when the projection portions are maximally protruded from the sheath.

2. The endoscope treatment system according to claim 1, wherein the engagement portions are slots that engage the projection portions in an inserted state.

3. The endoscope treatment system according to claim 1, wherein the projection portions and the engagement portions rotate in conjunction with the rotation operation of the insertion portion of the endoscope.

4. The endoscope treatment system according to claim 1, wherein the projection portions freely project and retract.

5. The endoscope treatment system according to claim 1, wherein the projection portions are conductive wires to which high-frequency electricity is supplied.

* * * * *